United States Patent [19]

Fialkov et al.

[11] 4,316,989
[45] Feb. 23, 1982

[54] PROCESS FOR PREPARING DIFLUOROMETHOXY DERIVATIVES OF AROMATIC ALDEHYDES

[76] Inventors: Jury A. Fialkov, ulitsa Oktyabrskoi Revoljutsii, 13/4, kv. 3; Svetlana V. Shelyazhenko, ulitsa Borschagovskaya, 10-a, kv. 141, both of Kiev, U.S.S.R.

[21] Appl. No.: 154,596

[22] Filed: May 29, 1980

[51] Int. Cl.$^3$ .............................................. C07C 45/61
[52] U.S. Cl. ................................................ 568/433
[58] Field of Search ........................ 568/433, 649, 655

[56] References Cited

U.S. PATENT DOCUMENTS

| | | | |
|---|---|---|---|
| 519,693 | 5/1894 | Bertram | 568/433 |
| 3,007,968 | 11/1961 | Alt | 568/433 |

OTHER PUBLICATIONS

Yagupolsky et al., USSR, Inventors Certificate 595,281, Mar. 23, 1978.
Houben–Weyl, Methoden der Organischen Chemie, vol. 4, No. 3, 24, 26, 27.
Geissman, Organic Reactions, vol. II, (1944), 94–97.
Henne et al., JACS, vol. 72 (1950), 4378–4380.
Hine et al. (I), JACS, vol. 79 (1957), 2654–2655.
Hine et al. (II), JACS, vol. 79 (1957), 5493–5496.

*Primary Examiner*—Bernard Helfin
*Attorney, Agent, or Firm*—Burgess, Ryan and Wayne

[57] ABSTRACT

A process for preparing difluoromethoxy derivatives of aromatic aldehydes having a common formula

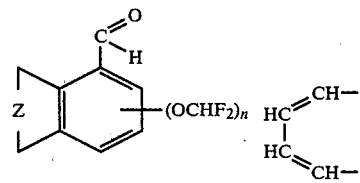

where Z is H,H; or
n is a whole number of 1 and 2.

The above process comprises the reaction between oxy derivatives of aromatic aldehydes selected from the group consisting of monooxy derivatives of aromatic aldehydes, and difluorochloromethane which reaction is carried out in an aqueous-dioxane medium at a temperature of 60° to 70° C., in the presence of 6 to 10 moles of caustic alkali per 1 mole of a starting oxyaldehyde.

6 Claims, No Drawings

PROCESS FOR PREPARING DIFLUOROMETHOXY DERIVATIVES OF AROMATIC ALDEHYDES

BACKGROUND OF THE INVENTION

1. Field of the Invention

The invention relates to a process for preparing difluoromethoxy derivatives of aromatic aldehydes and is useful in the chemical technology.

Difluoromethoxy derivatives of aromatic aldehydes are used in organic synthesis to obtain compounds possessing physiological activity. The scope of intended use of said compounds has not been yet exhausted. Difluoromethoxy derivatives of aromatic aldehydes may also be used for preparing dyes, pesticides etc. However, the complexity of the process of synthesizing said compounds does not allow these compounds to be used on a commercial scale. Therefore there is a problem of developing more straightforward processes for preparing difluoromethoxy derivatives of aromatic aldehydes.

2. Description of the Prior Art

Known in the art is a process for preparing derivatives of benzaldehyde containing difluoromethoxy-, difluoromethyl thio- or difluoromethylsulfonyl groups (USSR Inventor's Certificate No. 595281). Said compounds are prepared by treating an anilide of a corresponding substituted benzoic acid with phosphorus pentachloride, followed by reducing the resulting imido chloride with stannum dichloride in the medium of an anhydrous diethyl ether saturated with hydrogen chloride, and further hydrolyzing the reaction mixture with an aqueous solution of hydrochloric acid.

The yield of the end product is 77% calculated as the starting anilide. If the calculation is carried out on a hydroxybenzoic acid, the yield is 26 to 46%.

However, the process above described is complex and laborious. Besides, in the process of synthesis, a large amount of raw materials, such as aniline, phosphorus pentachloride, stannum dichloride saturated with hydrogen chloride, diethyl ether, hydrochloric acid, is used, thus involving considerable expenses to practice the process.

SUMMARY OF THE INVENTION

The principal object of the invention is to simplify the process for preparing difluoromethoxy derivatives of aromatic aldehydes with simultaneous increase in the yield of the end products.

Another object of the invention is to reduce expenses of raw materials per unit of the end product.

The objects set forth are attained in that the process for preparing difluoromethoxy deivatives of aromatic aldehydes having a structural formula

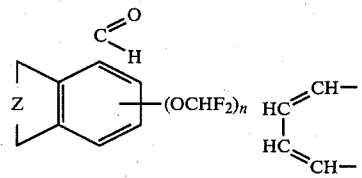

where Z is H,H; or
n is a whole number of 1 and 2,
which process, according to the invention, consists in that mono or dihydroxy derivatives of aromatic aldehydes are contacted with difluorochloromethane in an aqueous-dioxane medium at at a temperature of 60° to 70° in the presence of 6 to 10 moles of caustic alkali per 1 mole of starting oxyaldehyde.

The above process makes it possible to simplify the synthesis of difluoromethoxy derivatives of aromatic aldehydes with a simultaneous increase in the yield of the end product. This is due to the fact that during difluoromethylation of aromatic hydroxyaldehydes in an aqueous-dioxane solution in the presence of an excess of caustic alkali, the products of difluoromethylation practically are not involved in Cannizzaro's reaction, i.e. redox disproportionation is eliminated.

In the course of difluoromethylation which is carried out in the dioxane-water system, at first interaction takes place between difluorochloromethane and caustic alkali which is used in an amount of 6 to 10 moles per 1 mole of starting oxyaldehyde; this interaction leads to formation of a reactive particle which is difluorocarbene.

Considerable amounts of mineral salts are formed as a result of this reaction, these salts being mainly sodium fluoride, which leads to salting-out dioxane from the aqueous solution. Thus, as early as the beginning of difluoromethylation, the reaction mixture separates into two layers, a lower layer being an aqueous one and containing an anion of starting oxyaldehyde, the nonorganic compounds which are caustic alkali and salts, and an upper layer being dioxane whereto the formed end product is transferred. The fact that the formed difluoromethoxy derivatives of aromatic aldehydes are found in the dioxane layer makes it possible to decrease the contact between the end product and caustic alkali which contact can initiate redox disproportionation.

Besides, the specified process allows expenses of raw materials per unit of the end product to be decreased.

It is expedient to carry out the interaction between hydroxy derivatives of aromatic aldehydes and difluorochloromethane in the presence of dihydrate of sodium hydrosulfite in an amount of 0.3 to 0.4 moles per 1 mole of the starting oxyaldehyde.

Said modification of the process makes it possible to inhibit side reactions of oxidating starting substances and the end product with difluorocarbene.

DETAILED DESCRIPTION OF THE INVENTION

The process for preparing difluoromethoxy derivatives of aromatic aldehydes is carried out in a four-mouth flask having a capacity of 0.25 to 1.0 l and provided with a stirrer, a thermometer, a backflow condenser and a bubble flask intended for introducing a difluorochloromethane gas (commercially known as Freon-22). To control the flow of difluoromethylation reaction, Drexel or Tishchenko bottles filled with water, are placed before the bubble flask, i.e. at the flask inlet, and at the flask outlet, i.e. after the backflow condenser.

Prior to the beginning of the process, a corresponding mono or dihydroxy derivative of an aromatic aldehyde, for example, a salicylaromatic aldehyde, or p-hydroxybenzaldehyde, or 2,4-dihydroxybenzaldehyde, or 2-hydroxynaphthaldehyde, and dioxane, water, and caustic alkali taken in calculated amounts to form a reaction mixture, are put into the flask.

Synthesis may also be carried out in the presence of a dihydrate of a sodium hydrosulfite. The flask containing the reaction mixture is heated on a water bath until the temperature of the reaction mixture reaches 60° to 70° C. Freon-22 is fed to the flask at such a rate that in the Drexel or Tishchenko bottle which is placed at the outlet of an apparatus, after the backflow condenser, gas bubbles are not detected. The end of the process is defined when in the Drexel or Tishchenko bottle which is placed at the flask outlet, the rate of gas flow is the same as that at the flask inlet. After the process is over, the reaction mixture is cooled down to a temperature of 15° to 20° C., passed through a straining funnel to separate a sediment of mineral salts (sodium fluorides and chlorides). The sediment is then washed with a diethyl ether, and the aqueous-dioxane filtrate is diluted with water.

The dilution of the reaction mixture with water may be carried out directly after cooling down thereof. The aqueous-dioxane filtrate diluted with water is extracted with a diethyl ether, and an ether extract formed after washing the sediment of mineral salts is added to the obtained extract. The ether extract thus obtained is washed with a 10% aqueous solution of caustic alkali and then with water till the neutral reaction with subsequent drying using magnesium sulfate. When magnesium sulfate is separated, the ether is distilled and the residue is either distilled in vacuum or crystallized (the latter operation is carried out in the case of formation of solid products of difluoromethylation).

To estimate the properties of synthesized difluoromethoxy derivatives of aromatic aldehydes and to prove the presence of formyl group therein, said aldehydes are used to obtain corresponding crystalline 2,4-dinitrophenylhydrazones using a conventional method. To estimate liquid difluoromethoxy derivatives of aromatic aldehydes, the refraction index $n_D{}^t$ (the refraction index at a temperature t, determined on a dual spectrum line "D" of sodium) is determined using a standard refractometer.

The process of the invention will now be explained by way of specific Examples.

EXAMPLE 1

A process for preparing difluoromethoxy derivatives of aromatic aldehydes is carried out, according to the invention, as follows.

To a four-mouth flask having a capacity of 1 l and provided with a stirrer, a thermometer, a backflow condenser and a bubble flask, were added 30.5 g (0.25 g-mole) of salicyl aldehyde, 175 ml of water and 60 g (1.5 g-mole) of sodium hydrate to obtain a reaction mixture. Then the reaction mixture was heated with stirring on a water bath up to a temperature of 60° C., and at this temperature, a difluorochloromethane gas (Freon-22) was passed from a vessel through the bubble flask for 4 hours. After the process of difluoromethylation had been over, the above reaction mixture was cooled down to a temperature of 15° C. The residue of mineral salts (sodium fluorides and chlorides) was separated by means of a straining funnel and thoroughly pressed. The residue on the filter was washed 3 times with a diethyl ether, in a 40 ml quantity each time, and the aqueous-dioxane filtrate was poured into 800 ml of water. The mixture of water and the aqueous-dioxane filtrate was sequentially extracted 3 times with portions each containing 150 ml of a diethyl ether, shaking the above mixture on the straining funnel. Said ether extracts were mixed with an ether extract formed after washing the residue of the mineral salts. The ether extract thus obtained was twice treated with portions each containing 100 ml of a 10% aqueous solution of sodium hydrate and further washed with water till the neutral reaction and later dried with an anhydrous magnesium sulfate. After the magnesium sulfate had been separated, the ether was distilled and the residue was subjected to vacuum distillation.

The yield of o-difluoromethoxybenzaldehyde was 38.7 g (90%). The boiling point of o-difluoromethoxybenzaldehyde is 89° C. under a pressure of 5 mm Hg. $n_D{}^{20}$—1.4940.

Obtained by a conventional method 2,4-dinitrophenylhydrazone of o-difluoromethoxybenzaldehyde has the melting point of 198° to 199° C. (from a glacial acetic acid).

Anal. Calcd. for $C_{14}H_{10}F_2N_4O_5$, % C, 47.72; H, 2.84; F, 10.79; N, 15.90. Found, % C, 47.56; H, 2.76; F, 10.66; N, 15.98.

EXAMPLE 2

A process for preparing difluoromethoxy derivatives of aromatic aldehydes is carried out, according to the invention, as follows.

To a four-mouth flask having a capacity of 1 l and provided with a stirrer, a thermometer, a backflow condenser and a bubble flask, were added 30.5 g (0.25 g-mole) of p-hydroxybenzaldehyde, 175 ml of dioxane, 175 ml of water, and 60 g (1.5 g-mole) of caustic alkali to obtain a reaction mixture. Then the reaction mixture was heated with stirring on a water bath up to a temperature of 65° C., and at this temperature a difluorochloromethane gas (Freon-22) was passed from a vessel through the bubble flask for 5 hours. After the process of difluoromethylation had been over, the above reaction mixture was cooled down to a temperature of 15° C. The residue of mineral salts (sodium fluorides and chlorides) was separated by means of a straining funnel and thoroughly pressed. The residue on the filter was washed 3 times with a diethyl ether, in a 40 ml quantity each time, and the aqueous-dioxane filtrate was poured into 800 ml of water. The mixture of water and the aqueous-dioxane filtrate was sequentially extracted 3 times with portions each containing 150 ml of a diethyl ether, shaking the above mixture on the straining funnel. Said ether extracts were mixed with an ether extract formed after washing the residue of the mineral salts. The ether extract thus obtained was twice treated with portions each containing 100 ml of a 10% aqueous solution of caustic alkali and further washed with water till the neutral reaction and later dried with an anhydrous magnesium sulfate. After the magnesium sulfate had been separated, the ether was distilled and the residue was subjected to vacuum distillation.

The yield of p-difluoromethoxybenzaldehyde was 28 g (65%). The boiling point of p-difluoromethoxybenzaldehyde is 97° to 98° C. under a pressure of 5 mm Hg. $n_D{}^{20}$—1.5020.

Obtained by a conventional method, a sample of 2,4-dinitrophenylhydrazone of p-difluoromethoxybenzaldehyde has the melting point of 232° to 234° C. (from a glacial acetic acid).

Anal. Calcd. for $C_{14}H_{10}F_2N_4O_5$, % C 47.72, H 2.84, F 10.79, N 15.90; Found, % C, 47.62; H, 2.78; F, 10.76; N, 15.83.

EXAMPLE 3

A process for preparing difluoromethoxy derivatives of aromatic aldehydes is carried out, according to the invention, as follows.

To a four-mouth flask having a capacity of 0.25 l and provided with a stirrer, a thermometer, a backflow condenser and a bubble flask, were added 4.42 g (0.032 g-mole) of 2,4-dihydroxybenzaldehyde, 35 ml of dioxane, 35 ml of water and 19.8 g (0.32 g-mole) of caustic alkali, and 2 g (0.01 g-mole) of a dihydrate of a sodium hydrosulfite to obtain a reaction mixture. Then the reaction mixture was heated with stirring on a water bath up to a temperature of 70° C., and at this temperature a difluorochloromethane gas (Freon-22) was passed from a vessel through the bubble flask for 4 hours. After the process of difluoromethylation had been over, the above reaction mixture was cooled down to a temperature of 15° C. and was poured into 200 g of water and ice. The mixture of water and the aqueous dioxane filtrate was sequentially extracted 3 times with portions each containing 40 ml of a diethyl ether, shaking the above mixture on the straining funnel. Said ether extracts were mixed and were twice treated with portions each containing 20 ml of a 10% aqueous solution of caustic alkali and further washed with water till the neutral reaction and later dried with an anhydrous magnesium sulfate. After the magnesium sulfate had been separated, the ether was distilled, and 2,4-bis(difluoromethoxy)benzaldehyde which is difficult to be cleaned from admixtures, was separated and identified in the form of 2,4-dinitrophenylhydrazone obtained by a conventional method. The yield of 2,4-dinitrophenylhydrazone of 2,4-bis(difluoromethoxy)benzaldehyde was 8.41 g which yield calculated as 2,4-bis(difluoromethoxy)benzaldehyde is 63%. The melting point of 2,4-dinitrophenylhydrazone of 2,4-bis(difluoromethoxy)benzaldehyde is 188° to 189° C. (from a glacial acetic acid).

Anal. Calcd. for $C_{15}H_{10}F_4N_4O_6$, % C, 43.06; H, 2.39; F, 18.18; N 13.39; Found, %: C 42.96; H, 2.18; F 18.46; N, 13.33.

EXAMPLE 4

A process for preparing difluoromethoxy derivatives of aromatic aldehydes is carried out, according to the invention, as follows.

To a four-mouth flask having a capacity of 0.25 l and provided with a stirrer, a thermometer, a backflow condenser and a bubble flask, were added 6.9 g (0.04 g-mole) of 2-hydroxynaphthaldehyde, 30 ml of dioxane, 30 ml of water, 12.8 g (0.32 g-mole) of caustic alkali and 3 g (0.015 g-mole) of a dihydrate of a sodium hydrosulfite to obtain a reaction mixture. Then the reaction mixture was heated with stirring on a water bath up to a temperature of 70° C., and at this temperature a difluorochloromethane gas (Freon-22) was passed from a vessel through the bubble flask for 4 hours. After the process of difluoromethylation had been over, the above reaction mixture was cooled down to a temperature of 15° C. and was poured into 200 g of water and ice. The mixture of water and the aqueous dioxane filtrate thus obtained, was sequentially extracted 3 times with portions each containing 40 ml of a diethyl ether, shaking the above mixture on the straining funnel. Said ether extracts were mixed and were treated with portions each containing 10 ml of a 10% aqueous solution of caustic alkali and further washed with water till the neutral reaction and later dried with an anhydrous magnesium sulfate. After the magnesium sulfate had been separated, the ether was distilled, and the residue was crystallized from a mixture of benzene and hexane. The yield of 2-difluoromethoxynaphthaldehyde was 6.52 g (73.2%). The melting point of 2-difluoromethoxynaphthaldehyde is 112° to 114° C.

Obtained by a conventional method, 2,4-dinitrophenylhydrazone of 2-difluoromethoxynaphthaldehyde has the melting point of 224° to 227° C. (from a glacial acetic acid).

Anal. Calcd. for $C_{18}H_{12}F_2N_4O_5$, %: C, 53.73; H, 2.98; F, 9.45; N 13.93. Found, %: C, 53.63; H, 2.81; F, 9.36; N, 13.92.

EXAMPLE 5 (COMPARATIVE)

To a four-mouth flask having a capacity of 1 l and provided with a stirrer, a thermometer, a backflow condenser and a bubble flask, were added 30.5 g (0.25 g-mole) of salicyl aldehyde, 175 ml of dioxane, 175 ml of water and 30 g (0.75 g-mole) of caustic alkali to obtain a reaction mixture. Then the reaction mixture was heated with stirring on a water bath up to a temperature of 60° C., and at this temperature a difluorochloromethane gas (Freon-22) was passed from a vessel through the bubble flask for 4 hours. After the process of difluoromethylation had been over, the above reaction mixture was cooled down to a temperature of 15° C. The residue of mineral salts (sodium fluorides and chlorides) was filtered on a straining funnel and thoroughly pressed. The residue was washed 3 times with a diethyl ether, in a 40 ml quantity each time, and the aqueous-dioxane filtrate was poured into 800 ml of water. The mixture of water and the aqueous-dioxane filtrate thus obtained, was sequentially extracted 3 times with portions each containing 150 ml of a diethyl ether, shaking the above mixture on the straining funnel. Said ether extracts were mixed with an ether extract formed after washing the residue of mineral salts, and the ether extracts thus compounded were twice treated with portions each containing 100 ml of a 10% aqueous solution of caustic alkali and further washed with water till the neutral reaction and later dried with an anhydrous magnesium sulfate. After the magnesium sulfate had been separated, the ether was distilled and the residue was subjected to vacuum distillation.

The yield of the end product which was o-difluoromethoxybenzaldehyde, was 19.2 g or 45% of the precalculated value.

Thus a decrease in an amount of caustic alkali below the specified range leads to a decrease in the yield of the end product by 50%, that is said yield is 2 times reduced.

EXAMPLE 6 (COMPARATIVE)

To a four-mouth flask having a capacity of 1 l and provided with a stirrer, a thermometer, a backflow condenser and a bubble flask, were added 30.5 g (0.25 g-mole) of salicylaldehyde, 175 ml of dioxane, 175 ml of water and 60 g (1.5 g-mole) of caustic alkali to obtain a reaction mixture. Then the reaction mixture was heated with stirring on a water bath up to a temperature of 35° C., and at this temperature a difluorochloromethane gas (Freon-22) was passed from a vessel through the bubble flask for 4 hours. After the process of difluoromethylation had been over, the above reaction mixture was cooled down to a temperature of 15° C. The residue of mineral salts (sodium fluorides and chlorides) was filtered on a straining funnel and thoroughly pressed. The residue was washed 3 times with a diethyl ether, in a 40 ml quantity each time, and the aqueous-dioxane filtrate was poured into 800 ml of water. The mixture of water and the aqueous-dioxane filtrate thus obtained, was sequentially extracted 3 times with portions each containing 150 ml of a diethyl ether, shaking the above mixture on the straining funnel. Said ether extracts were mixed with an ether extract formed after washing the residue of mineral salts, and the ether extracts thus compounded were twice treated with portions each containing 100 ml of a 10% aqueous solution of caustic alkali and further washed with water till the neutral reaction and later dried with an anhydrous magnesium sulfate. After the magnesium sulfate had been separated, the ether was distilled and the residue was subjected to vacuum distillation.

The yield of the end product which was o-difluoromethoxybenzaldehyde, was 25.6 g or 60% of the precalculated value.

Thus a decrease in the reaction temperature results in a decrease in the yield of the end product.

EXAMPLE 7 (COMPARATIVE)

To a four-mouth flask having a capacity of 1 l and provided with a stirrer, a thermometer, a backflow condenser and a bubble flask, were added 30.5 g (0.25 g-mole) of salicyl aldehyde, 175 ml of dioxane, 175 ml of water and 60 g (1.5 g-mole) of caustic alkali to obtain a reaction mixture. Then the reaction mixture was heated with stirring on a water bath up to a temperature of 100° C., and at this temperature a difluorochloromethane gas (Freon-22) was passed from a vessel through the bubble flask for 4 hours. After the process of difluoromethylation had been over, the above reaction mixture was cooled down to a temperature of 15° C. The residue of mineral salts (sodium fluorides and chlorides) was filtered on a straining funnel and thoroughly pressed. The residue was washed 3 times with a diethyl ether, in a 40 ml quantity each time, and the aqueous-dioxane filtrate was poured into 800 ml of water. The mixture of water and the aqueous-dioxane filtrate thus obtained, was sequentially extracted 3 times with portions each containing 150 ml of a diethyl ether, shaking the above mixture on the straining funnel. Said ether extracts were mixed with an ether extract formed after washing the residue of mineral salts, and the ether extracts thus compounded were twice treated with portions each containing 100 ml of a 10% aqueous solution of caustic alkali and further washed with water till the neutral reaction and later dried with an anhydrous magnesium sulfate. After the magnesium sulfate had been separated, the ether was distilled and the residue was subjected to vacuum distillation.

The yield of the end product which was p-difluoromethoxybenzaldehyde, was 23.6 g or 55% of the precalculated value.

The product is colored and is difficult to be separated from resinous admixtures.

Thus an increase in a reaction temperature above the specified range results in a decrease in the yield of the end product and in a quality deterioration thereof.

While the invention has been described herein in terms of specific Examples, numerous variations and modifications may be made in the invention without departing from the spirit and scope thereof as set forth in the appended claims.

What is claimed is:

1. A process for preparing difluoromethoxy derivatives of aromatic aldehydes having a common formula:

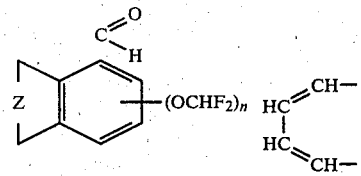

where Z is H,H; or
n is 1 or 2,
said process comprising reacting a hydroxy derivative of an aromatic aldehyde selected from the group consisting of mono-hydroxy derivatives of aromatic aldehydes and dihydroxy derivatives of aromatic aldehydes, with difluorochloromethane in an aqueous-dioxane medium at a temperature of 60° to 70° C., in the presence of 6 to 10 moles of caustic alkali per 1 mole of a starting hydroxyaldehyde.

2. A process as set forth in claim 1, wherein the reaction between the above hydroxy derivative of the aromatic aldehydes and the difluorochloromethane is carried out in the presence of 0.3 to 0.4 moles of a dihydrate of a sodium hydrosulfite per 1 mole of the above starting hydroxyaldehyde.

3. The process of claims 1 or 2 wherein the hydroxy derivative of an aromatic aldehyde is salicylaldehyde.

4. The process of claims 1 or 2 wherein the hydroxy derivative of an aromatic aldehyde is p-hydroxybenzaldehyde.

5. The process of claims 1 or 2 wherein the hydroxy derivative of an aromatic aldehyde is a dihydroxybenzaldehyde.

6. The process of claims 1 or 2 wherein the hydroxy derivative of an aromatic aldehyde is 2-hydroxynaphthaldehyde.

* * * * *